(12) United States Patent
Seth

(10) Patent No.: US 7,605,173 B2
(45) Date of Patent: Oct. 20, 2009

(54) PHARMACEUTICAL LIQUID COMPOSITION CONTAINING PYRIDONE DERIVATIVE

(75) Inventor: Pyare L. Seth, Basel (CH)

(73) Assignee: KDL, Inc., Tokyo (JP)

( * ) Notice: Subject to any disclaimer, the term of this patent is extended or adjusted under 35 U.S.C. 154(b) by 0 days.

(21) Appl. No.: 10/540,422

(22) PCT Filed: Dec. 24, 2003

(86) PCT No.: PCT/JP03/16599

§ 371 (c)(1),
(2), (4) Date: Apr. 4, 2006

(87) PCT Pub. No.: WO2004/058256

PCT Pub. Date: Jul. 15, 2004

(65) Prior Publication Data

US 2006/0167064 A1 Jul. 27, 2006

(30) Foreign Application Priority Data

Dec. 26, 2002 (JP) ............................. 2002-375834

(51) Int. Cl.
*A61K 31/44* (2006.01)
*A61K 31/522* (2006.01)

(52) U.S. Cl. .................. 514/345; 514/263.31; 514/969; 514/327; 546/280.4; 544/168

(58) Field of Classification Search ........................ None
See application file for complete search history.

(56) References Cited

U.S. PATENT DOCUMENTS

| | | | | | |
|---|---|---|---|---|---|
| 3,839,346 | A | * | 10/1974 | Gadegar | 546/249 |
| 6,492,395 | B1 | * | 12/2002 | Scheiwe et al. | 514/327 |
| 2004/0033257 | A1 | * | 2/2004 | Iyer et al. | 424/456 |
| 2006/0039931 | A1 | * | 2/2006 | Scheiwe et al. | 424/400 |

FOREIGN PATENT DOCUMENTS

| | | | |
|---|---|---|---|
| GB | 1529960 | A | 10/1978 |
| WO | WO 94/26249 | * | 11/1994 |
| WO | WO 99/47140 | A1 | 9/1999 |
| WO | WO 00/41692 | A1 | 7/2000 |
| WO | WO 01/47495 | A1 | 7/2001 |
| WO | WO 01/58448 | A1 | 8/2001 |
| WO | WO 01/78724 | A1 | 10/2001 |

* cited by examiner

*Primary Examiner*—Frederick Krass
*Assistant Examiner*—Lezah W Roberts
(74) *Attorney, Agent, or Firm*—Sughrue Mion, PLLC

(57) ABSTRACT

A pharmaceutical liquid composition containing the Pirfenidone in a very high concentration of more or less 25% by weight can be obtained by dissolving the Pirfenidone in diethylene glycol monoethyl ether. Even when the liquid medicinal compositions are stored for a long period of time, the Pirfenidone will not be recrystallized with a good chemical and physical stability. Furthermore, the liquid compositions are little irritating to the wounds on the mucous membrane of the skin and suitable for the manufacture of pharmaceutical formulations to be administered either via the oral, percutaneous, nasal or vaginal routes or by means of spray, patch, inhalation, injection or intravenous drip.

11 Claims, No Drawings

PHARMACEUTICAL LIQUID COMPOSITION CONTAINING PYRIDONE DERIVATIVE

TECHNICAL FIELD

The present invention relates to a pharmaceutical liquid composition containing a pyridone derivative. More particularly, it relates to a pharmaceutical liquid composition containing as the active ingredient a pyridone derivative such as 5-methyl-1-phenyl-2-(1H)-pyridone (Pirfenidone) and the like, which is effective in the treatment of dermatological disorders, particularly fibrotic dermatoses such as fibrotic lesional tissues, contiguous warts and the like or contact dermatitis, keloids, scars after burn surgery and the like. Said liquid compositions containing the pyridone derivative in the high concentrations, with the absence of recrystallization is stable for a long period of time and suitable to be administered orally, percutaneously, nasally or vaginally or as a spray, patch, inhalant, injection or intravenous drip.

BACKGROUND OF THE INVENTION

As described in U.S. Pat. No. 5,310,562 and European Laid-Open Patent No. 0383591, the 5-methyl-1-phenyl-2-(1H)-pyridone (Pirfenidone) has found a broad spectrum of applications in the prevention and treatment of fibrotic disorders, particularly in the reparation and prevention of fibrotic lesional tissues, contiguous warts, contact dermatitis, keloids, fibrosis of the lung, fibrosis and hypertrophy of the prostate, nephrosclerosis and the like; and useful in the treatment of scars after burn surgery, Alzheimer's disease and the like. These literatures have described that the Pirfenidone is generally administered orally or percutaneously or by injection.

With respect to the Pirphenidone pharmaceutical formulations, International Published Application WO00/16775 has described a gel formulation for topical administration, comprising a gel-forming agent such as carboxypolymethylene, a plasticizer such as polypropylene, an antioxidant such as sodium metabisulfite and a pH adjusting agent such as sodium hydroxide. The gel formulation has been described as excellent in stability without the recrystallization of the active ingredient even after it is stored at various temperatures for a long period of time. However, the highest possible concentration of active ingredient is 7% by weight in these gel formulations and it cannot be said that the formulations are capable of containing the active ingredient in a sufficiently high concentration.

Attempts to make the highly concentrated formulations by using alcohol-based solvents as the solution-forming agent would be frustrated because the solvents irritate the mucous membrane, give rise to pains in open wounds and are not acceptable clinically. In Europe and USA, dimethylsulfoxide (DMSO) has been incorporated into the pharmaceutical formulations for external use as the additive unaccompanied by irritation to the mucous membrane and capable of increasing the solubility of Pirfenidone. However, the DMSO has been found to be problematical from the viewpoint of safety.

DISCLOSURES OF THE INVENTION

Thus, it has been desired to develop a liquid pharmaceutical formulation capable of containing Pirfenidone as the active ingredient in a high concentration, with the absence of recrystallization during the longtime storage, stable chemically and physically and suitable to be administered either orally, percutaneously, nasally or vaginally or as a spray, patch, inhalant, injection or intravenous drip without causing any problems from the viewpoint of safety.

An intensive investigation was conducted with a view to finding a means for solving the above-mentioned problems. As a result, it has been found that a pharmaceutical liquid composition comprising Pirfenidone in a high concentration of more or less 25% by weight can be obtained by dissolving the active ingredient in a diethylene glycol monoethyl ether that is a medical solvent called Transcutol-P and described and its safety confirmed in the European and US pharmacopeias. It has also been found that the so obtained composition does not recrystallize if stored for a long period of time, able to be administered either orally, percutaneously, nasally or vaginally or as a spray, patch, inhalant, injection or intravenous drip and certain to make a pharmaceutical composition excellent in every point. The present invention has been brought to completion on the basis of these findings.

The present invention provides a pharmaceutical liquid composition comprising as an active ingredient a pyridone derivative represented by the following formula (I):

wherein $R^1$ is an alkyl group optionally having a substituent and $R^2$ is a phenyl group optionally having a substituent or a pharmaceutically acceptable salt thereof, and a solvent capable of dissolving said active ingredient in a high concentration.

BEST MODE FOR CARRYING OUT THE INVENTION

The pharmaceutical liquid composition of the present invention comprises as the active ingredient a pyridone derivative represented by the above-mentioned formula (I) or a pharmaceutically acceptable salt thereof. In the above-mentioned formula (I), $R^1$ is an alkyl group optionally having a substituent and $R^2$ is a phenyl group optionally having a substituent. The examples of the alkyl group optionally having a substituent as $R^1$ include a $C_{1-6}$ lower alkyl group such as methyl, ethyl, propyl, isopropyl, butyl, isobutyl, pentyl or hexyl and an alkyl group having a substituent in which said lower alkyl group is substituted with a halogen atom such as fluorine or chlorine; a carboxyl group; an alkoxycarbonyl group such as methoxycarbonyl or ethoxycarbonyl; or a substituent such as amino group. The alkyl group optionally having a substituent as $R^1$ may be substituted at any of the 3-position, 4-position or 5-position. The examples of the phenyl group optionally having a substituent as $R^2$ include a phenyl group and a phenyl group having a substituent in which the phenyl group is substituted with a $C_{1-6}$ lower alkyl group such as methyl, ethyl, propyl, isopropyl, butyl, isobutyl, pentyl or hexyl; a halogen atom such as fluorine or chlorine; a carboxyl group; an alkoxycarbonyl group such as methoxycarbonyl or ethoxycarbonyl; or a substituent such as amino group.

For the pyridone derivative as the active ingredient, it is preferable to use the 5-methyl-1-phenyl-2-(1H)-pyridone (Pirfenidone) wherein $R^1$ is a methyl group substituted at the 5-position and $R^2$ is a phenyl group.

The pyridone derivative as the active ingredient may be a pharmaceutically acceptable salt thereof. The examples of the salt include an acid addition salt, a salt with alkali or the like. The example of the acid addition salt include an acid addition salt with an acid such as hydrochloric acid, sulfuric acid, phosphoric acid, paratoluene sulfonic acid or methane sulfonic acid. The example of the salt with alkali includes a salt such as sodium salt or potassium salt.

In the liquid composition of the present invention, it is preferable to use the diethylene glycol monoethyl ether (also known as ethoxy diglycol or diethylene glycol ethyl ether) as the solvent capable of dissolving the active ingredient in a high concentration. The diethylene glycol monoethyl ether is a compound represented by the following chemical formula:

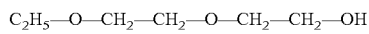

$C_2H_5-O-CH_2-CH_2-O-CH_2-CH_2-OH$

According to the 3rd and 4th editions of European Pharmacopoeia, the compound occurs as colorless and transparent, well miscible with water, and has been marketed by the name of Transcutol P as a commonly used solvent. It has also been known that the compound can be used as an absorption promoter in medicine (Ritschel, W. et al., Skin Pharmacol., (1191) 4, 235-245). In the present invention, it is preferable to use the diethylene glycol monoethyl ether having a purity of 99% or higher, more preferably 99.7% or higher and most preferably 99.9% or higher.

The present invention has demonstrated that the Pirfenidone can be dissolved in a very high concentration of more or less 25% by weight by selecting the diethylene glycol monoethyl ether among others as the solvent for Pirfenidone and thus that a liquid medicinal composition containing the Pirfenidone in a very high concentration can be obtained. This high concentration corresponds to the 300 mg dose of the drug in a solution of 2 ml, almost equivalent to the dosage of the same drug in common tablets presently used for oral administration.

In addition to the pyridone derivative, for example, Pirfenidone as the active ingredient and the diethylene glycol monoethyl ether as the solvent, the liquid medicinal composition of the present invention can contain a concentrating agent, antioxidant, dispersant, viscosity adjusting agent, diluent, antimicrobial and the like that are commonly used in medicinal formulations, depending upon the method of administration, the route of administration, the specific type of formulation and the like. The examples of the concentrating agent include polyvinyl pyrrolidone, hydroxypropyl cellulose, hydroxypropyl methyl cellulose and the like. The examples of the antioxidant include sodium metabisulfite, α-tocopherol, sodium ascorbate and the like. The examples of the dispersant include polyvinyl pyrrolidone, hydroxypropyl cellulose, hydroxypropyl methyl cellulose, methyl cellulose, ethyl cellulose and the like. The examples of the viscosity adjusting agent include bentonite, calcium magnesium silicate and the like. The examples of the diluent include methanol, ethanol and the like. The examples of the antimicrobial include benzalkonium chloride, benzethonium chloride, methylparaben, ethylparaben and the like.

The liquid composition of the present invention has a broad spectrum of application in the administration via oral, percutaneous, nasal or vaginal routes or by means of spray, patch, inhalation, injection or intravenous drip and the like. For example, the highly concentrated solution dissolving the pyridone derivative such as Pirfenidone in the solvent comprising diethylene glycol monoethyl ether is partially separated and the so separated liquid is diluted with water or fruit juice to make a pharmaceutical formulation for oral administration. The liquid composition of the present invention dissolves in a high concentration Pirfenidone which is slightly soluble in water by nature, accompanied by the hydration property permitting the composition to be diluted 4 to 5 times with water and make a pharmaceutical formulation for oral administration with ease. Furthermore, the liquid composition of the present invention is very low in viscosity and can be filled into a pump spray as a spray formulation or into a roll-on container for use in oral, nasal or vaginal administration. Moreover, it also can be filled into, for example, a vaporizer such as nebulizer, to make a pharmaceutical formulation for vaporizing administration. Furthermore, an injection or intravenous drip can be prepared from the composition by adding isotonic physiological saline thereto.

With respect to the liquid composition of the present invention, the preferred specific examples will be shown below:

| Ingredients | % by weight |
| --- | --- |
| Pirfenidone | 1-25 |
| Diethylene glycol monoethyl ether | 70-80 |
| Ethanol (95%) | 0-10 |
| Polyvinyl pyrrolidone or hydroxypropyl cellulose | 0-3 |
| Sodium metabisulfite | 0.02-2 |
| Methyl or propyl paraben | 0-0.5 |
| Purified water | 0-25 |

| Ingredients | % by weight |
| --- | --- |
| Pirfenidone | 10-25 |
| Diehtylene glycol monoethyl ether | 75-80 |
| Purified water | 0-10 |

| Ingredients | % by weight |
| --- | --- |
| Pirfenidone | 10-25 |
| Diethylene glycol monoethyl ether | 75-80 |
| α-Tocopherol | 0.1-0.5 |
| Hydroxypropyle cellulose | 0-3 |
| Purified water | 0-10 |

The present invention will be explained in detail below, with reference to examples, but the present invention will not be limited by these examples in any way.

EXAMPLES 1 to 6

The pharmaceutical liquid compositions were prepared from the formulations listed in Table 1.

That is, the diethylene glycol monoethyl ether was charged to a suitable container and warmed to 60° C. The Pirfenidone was added while stirring and a yellowish solution was obtained by continuing the stirring until the mixture was transparent. All the remaining ingredients as listed in Table 1 were dissolved in water at 60° C. and this solution was poured into the above Pirfenidone solution and the stirring was continued until mixed uniformly. The so obtained solution was protected from the light. The solutions of Examples 1 and 2 were found to have the viscosity similar to that of water. It was found that the solution of Example 5 had the slightly higher viscosity but was not in a state of gel and still pourable, while, the solutions of Examples 3 and 4 were found to have the viscosity similar to that of water.

TABLE 1

| Ingredients | Example 1 | Example 2 | Example 3 | Example 4 | Example 5 | Example 6 |
| --- | --- | --- | --- | --- | --- | --- |
| Pirfenidone | 25.0 g | 10.0 g | 25.0 g | 10.00 g | 5.00 g | 5.00 g |
| Diethylene glycol monoethyl ether | 75.0 g | 80.0 g | 70.0 g | 80.00 g | 80.00 g | 80.00 g |
| Ethanol | | | | | 5.00 g | 5.00 g |
| Polyvinyl Pyrrolidone | | | | | 2.96 g | |
| Hydroxy propyl cellulose | | | | | | 2.96 g |
| Sodium metabisulfite | | | | 0.02 g | 0.02 g | 0.02 g |
| Methylparaben or propyl-Paraben | | | | 0.02 g | 0.02 g | 0.02 g |
| Purified water | | 10.0 g | 5.0 g | 9.96 g | 7.00 g | 7.00 g |
| Total weight | 100.0 g | 100.0 g | 100.00 g | 100.00 g | 100.00 g | 100.00 g |

As shown in Table 1, the liquid compositions containing the Pirfenidone in the high concentrations could be obtained by dissolving the Pirfenidone in the diethylene glycol monoethyl ether.

EXAMPLES 7 to 11

The liquid compositions were prepared, having the formulations listed in Table 2.

That is, the diethylene glycol monoethyl ether was charged to a suitable container and warmed to 60° C., and the Pirfenidone was added while stirring and a yellowish solution was obtained by continuing the stirring until the whole became transparent. Furthermore, the α-tocopherol was added and water was added while stirring until mixed uniformly. Then, the hydroxypropyl cellulose was added because of its necessity and stirred until a homogenous dispersion was formed. Furthermore, the dispersion was allowed to stand overnight until the particles of hydroxypropyl cellulose, the concentrating agent, were expanded, and finally the product was homogenized. The so obtained dispersion was allowed to stand overnight and a solution in the desired concentration was obtained. The solution was homogenized again and protected from light. The solutions of Examples 7 and 8 were found to have the viscosity similar to that of water.

TABLE 2

| Ingredients | Example 7 | Example 8 | Example 9 | Example 10 | Example 11 |
| --- | --- | --- | --- | --- | --- |
| Pirfenidone | 25.0 g | 10.0 g | 25.0 g | 25.0 g | 10.0 g |
| Diethylene glycol monoethyl ether | 74.0 g | 78.0 g | 73.8 g | 74.8 g | 80.0 g |
| α-Tocopherol | 1.0 g | 2.0 g | 0.2 g | 0.2 g | 0.2 g |
| Hydroxypropyl cellulose | | | 1.0 g | | |
| Purified water | | 10.0 g | | | |
| Total weight | 100.0 g | 100.0 g | 100.0 g | 100.0 g | 100.0 g |

As shown in Table 2, the liquid compositions containing the Pirfenidone in the high concentrations could be obtained by dissolving the Pirfenidone in diethylene glycol monoethyl ether.

INDUSTRIAL APPLICABILITY

As described above, the Pirfenidone is dissolved in diethylene glycol monoethyl ether, with the result that the liquid medicinal compositions containing the Pirfenidone in very high concentrations of more or less 25% by weight are obtained. When these liquid compositions are stored at low temperatures for a long period of time, the Pirfenidone will not be recrystallized with a good chemical and physical stability. The liquid compositions have a broad spectrum of application in manufacturing the various different pharmaceutical formulations for use in administration via oral, percutaneous, nasal or vaginal routes or by means of spray, patch, inhalation, Injection or intravenous drip. The liquid compositions can undergo the sterilization in the manufacturing process for injections or intravenous drips and are well miscible when they are diluted in water and non-irritating when applied to the open wounds. Even if the liquid medicinal compositions are contained in non-aqueous pharmaceutical formulations, they will be very stable, having many different advantages.

The invention claimed is:

1. A pharmaceutical liquid composition comprising 5-methyl-1-phenyl-2-(1H)-pyridone or a pharmaceutically acceptable salt thereof in a concentration of 10% to 25% by weight and dissolved in diethylene glycol monoethyl ether solvent, said composition comprising 70-80% by weight of said solvent.

2. A pharmaceutical liquid composition according to claim 1, wherein the diethylene glycol monoethyl ether has a purity of 99% or higher.

3. A pharmaceutical liquid composition according to claim 1, further comprising polyvinyl pyrrolidone, hydroxypropyl cellulose, or hydroxypropyl methyl cellulose.

4. A pharmaceutical liquid composition according to claim 1, further containing an antioxidant.

5. A pharmaceutical liquid composition according to claim 4, wherein the antioxidant is an α-tocopherol.

6. A pharmaceutical liquid composition according to claim 1, in the form of an oral, percutaneous, nasal or vaginal preparation or in the form of a spray, patch, inhalant, injection or intravenous drip.

7. A pharmaceutical liquid composition according to claim 1, having the following components:

| Ingredients | % by weight |
| --- | --- |
| methyl-1-phenyl-2-(1H)-pyridone | 10-25 |
| Diethylene glycol monoethyl ether | 70-80 |
| Ethanol (95%) | 0-10 |
| Polyvinyl pyrrolidone or hydroxypropyl cellulose | 0-3 |
| Sodium metabisulfite | 0.02-2 |
| Methyl or propyl paraben | 0-0.5 |
| Purified water | 0-25. |

8. A pharmaceutical liquid composition according to claim 1, having the following components:

| Ingredients | % by weight |
| --- | --- |
| methyl-1-phenyl-2-(1H)-pyridone | 10-25 |
| Diethylene glycol monoethyl ether | 75-80 |
| Purified water | 0-10. |

9. A pharmaceutical liquid composition according to claim 1, having the following components:

| Ingredients | % by weight |
| --- | --- |
| methyl-1-phenyl-2-(1H)-pyridone | 10-25 |
| Diethylene glycol monoethyl ether | 75-80 |
| α-Tocopherol | 0.1-0.5 |
| Hydroxypropyl cellulose | 0-3 |
| Purified water | 0-10. |

10. The pharmaceutical composition according to claim 1, wherein the composition is stable.

11. The pharmaceutical composition according to claim 1, wherein the composition does not cause skin irritation.

* * * * *